(12) United States Patent
Westernacher et al.

(10) Patent No.: US 6,225,512 B1
(45) Date of Patent: May 1, 2001

(54) METHOD FOR PRODUCING AND PURIFYING 3-(3-HYDROXYPHENYL)-1,1,3-TRIMETHYLINDAN-5-OL

(75) Inventors: Stefan Westernacher, Seabrook, TX (US); Franz Kosik, Kerken (DE); Wolfgang Calaminus, Krefeld (DE); Wilfried Haese, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/446,477

(22) PCT Filed: Jun. 22, 1998

(86) PCT No.: PCT/EP98/03801

§ 371 Date: Feb. 14, 2000

§ 102(e) Date: Feb. 14, 2000

(87) PCT Pub. No.: WO99/01415

PCT Pub. Date: Jan. 14, 1999

(30) Foreign Application Priority Data

Jul. 3, 1997 (DE) .............................................. 197 28 377

(51) Int. Cl.[7] .................................................. C07C 39/12
(52) U.S. Cl. ............................................................ 568/719
(58) Field of Search ............................................... 568/719

(56) References Cited

U.S. PATENT DOCUMENTS

| 2,754,285 | 7/1956 | Petropoulos | ............................ 260/47 |
|---|---|---|---|
| 2,819,249 | 1/1958 | Petropoulos et al. | ............. 260/45.95 |
| 2,979,534 | 4/1961 | Petropoulos et al. | ................. 260/619 |
| 3,264,357 | 8/1966 | Webb et al. | ........................... 260/619 |
| 3,264,358 | 8/1966 | Webb et al. | ........................... 260/619 |
| 3,271,463 | 9/1966 | Howard | ................................. 260/619 |
| 3,288,864 | * 11/1966 | Farnham | ............................... 568/719 |
| 4,201,877 | 5/1980 | Yamazaki et al. | .................... 568/720 |
| 5,994,596 | * 11/1999 | Chan | ..................................... 568/719 |

FOREIGN PATENT DOCUMENTS

| 2645020 | * 4/1978 | (DE) . |
| 5-294879 | 11/1993 | (JP) . |
| 6-35150 | 2/1994 | (JP) . |

OTHER PUBLICATIONS

Vogel, " A Text–book of Practical Organic Chemistry," 3rd. Ed., pp. 122–130, 1957.*

Ault, "Techniques and Experments for Organic Chemistry," 4th Ed., pp. 41–59, 1983.*

* cited by examiner

*Primary Examiner*—Michael L. Shippen
(74) *Attorney, Agent, or Firm*—Joseph C. Gil; Aron Preis

(57) ABSTRACT

A process is disclosed for the preparation and purification of 3-(4-hydroxyphenyl)-1,1,3-trimethylindan-5-ol. Accordingly, isopropenylphenol, its dimers or oligomers undergo isomerization in the presence of an acid catalyst, the reaction mixture is optionally neutralized by adding a base and 3-(4-hydroxyphenyl)-1,1,3-trimethylindan-5-ol is isolated by recrystallization.

2 Claims, No Drawings

METHOD FOR PRODUCING AND PURIFYING 3-(3-HYDROXYPHENYL)-1,1,3-TRIMETHYLINDAN-5-OL

The invention relates to an improved process for the preparation and purification of 3(4-hydroxyphenyl)-1,1,3-trimethylindan-5-ol by isomerisation of dimers or oligomers of isopropenylphenol and subsequent recrystallisation.

There are already several known processes for the preparation of 3-(4-hydroxyphenyl)-1,1,3-trimethylindan-5-ol, referred to below as bisphenol indan.

Thus U.S. Pat. No. 2,754,285 and U.S. Pat. No. 2,819,249 disclose a preparative route via the acid-catalysed dimerisation of α-methylstyrene to indans, which are subsequently sulfonated and then saponified with potassium hydroxide.

U.S. Pat. No. 2,979,534 discloses that the monomeric isopropenylphenols obtained by decomposition of bisphenols can be dimerised to bisphenol indan at temperatures of 110° C. to 160° C. in the presence of aromatic sulfonic acids or mineral acids. Bisphenol decomposition and indan formation can also be carried out in one step. This process yielded a product of low purity, which even after recrystallisation from benzene/cyclohexane had a melting point of only 165–166° C.

U.S. Pat. No. 3,264,357 discloses the preparation of bisphenols by reacting a mixture of the two isomeric forms of dimeric isopropenylphenol with phenols in the presence of strong acids. It is reported that bisphenol indan is formed at a reaction temperature of 90° C. in the absence of reactive phenols. According to U.S. Pat. No. 3,264,358, bisphenol indan can be obtained by reacting a mixture of the two isomeric forms of dimeric isopropenylphenol with strongly acidic catalysts, for example, by heating for two hours in concentrated hydrochloric acid at boiling heat.

U.S. Pat. No. 3,288,864 discloses the preparation of bisphenol indan by self-condensation of monomeric isopropenylphenol at temperatures of 50° C. to 150° C. in the presence of Friedel-Crafts catalysts; JP-A 60/35150 discloses the isomerisation of isopropenylphenol or of its oligomers in the presence of solid catalysts such as aluminium oxide or terra alba.

According to U.S. Pat. No. 4,334,106, bisphenol indan can be prepared by reacting isopropenylphenol or its oligomers in halogenated carboxylic acids or formic acid at temperatures of 0° C. to 90° C.

According to JP-A 5/294879, bisphenol indan can be obtained by thermal decomposition of bisphenol A in the presence of activated clay; U.S. Pat. No. 3,271,463 discloses the formation of bisphenol indan as a secondary product in the treatment of bisphenol A with aqueous sulfric acid at 90° C. to 150° C. In both processes relatively large quantities of spirobisindan bisphenol are formed, and these have to be separated from aromatic hydrocarbons by recrystallisation.

As regards the yields and the purity of the product, the processes described are in many cases still inadequate for an industrial production of bisphenol indan for use as starting material for the production of plastics. An improved process, whereby bisphenol indan can be prepared in high yield and purity, has now been found.

The invention provides a process for the preparation and purification of bisphenol indan, wherein first of all isopropenylphenol, its dimers or oligomers or mixtures of these are dissolved in an organic solvent, the boiling point of which is in the temperature range of 110° C. to 150° C., preferably 130° C. to 140° C., the reaction mixture is heated to a temperature within the range of 60° C. to 110° C., preferably 70° C. to 90° C., then 0.002 to 5 wt. %, preferably 0.3 to 0.5 wt. %, based on the quantity of isopropenylphenol used, of an acidic catalyst is added optionally in portions, the reaction mixture is heated to boiling and allowed to react at the boiling temperature for 1 to 600 minutes, preferably 2 to 60 minutes, then the reaction mixture is optionally neutralised at a temperature within the range of 60° C. to 100° C., preferably 70° C. to 90° C., by addition of a base, then water is added to the reaction mixture and the latter is cooled to a temperature within the range of 0° C. to 30° C., preferably 0° C. to 10° C., the precipitate formed is separated off, dried and recrystallised from an acetic acid/water mixture.

The starting materials used for the process according to the invention are isopropenyl-phenol, its dimers or oligomers. The dimers and oligomers are easily accessible and can be prepared, for example, by the methods described in U.S. Pat. No. 3,288,864 or U.S. Pat. No. 4,201,877.

In the process according to the invention, the solvents used are those organic solvents which have a boiling point in the temperature range of 110° C. to 150° C., preferably 130° C. to 140° C. Examples are toluene, n-butanol, chlorobenzene and xylene; chlorobenzene is preferably used. The quantity of solvent is preferably two to three times the quantity of isopropenylphenol used.

After the reaction mixture has been heated to a temperature within the range of 60° C. to 110° C., preferably 70° C. to 90° C., an acidic catalyst is added thereto in a quantity of 0.002 to 5 wt. %, preferably 0.3 to 0.5 wt. %, based on the quantity of isopropenylphenol used. Bronstedt acids or Lewis acids can be used as catalysts for the process according to the invention. Examples are mineral acids such as hydrochloric acid or sulfuric acid, organic acids such as sulfonic acids or halogenated carboxylic acids, acidic ion-exchange resins, boron trifluoride and metal halides such as $AlCl_3$, $FeCl_3$ or $ZnCl_2$. Preferably Lewis acids are used as catalysts, particularly preferably boron trifluoride.

After the addition of the catalyst, the reaction mixture is heated to boiling and allowed to react at boiling temperature for 1 to 600 minutes, preferably 2 to 60 minutes. It has become apparent that, at temperatures within the range of 110° C. to 150° C., in particular 130° C. to 140° C., the isomerisation reaction leads to bisphenol indan with particularly high selectivity.

Optionally the reaction mixture is then neutralised at a temperature within the range of 60° C. to 100° C., preferably 70° C. to 90° C., by addition of a base. A multitude of different bases or mixtures thereof are suitable for this. Examples are metal hydroxides such as NaOH, KOH, $Mg(OH)_2$, $Ca(OH)_2$, alkoxides such as sodium methoxide, sodium ethoxide, sodium phenoxide, potassium methoxide, potassium ethoxide, potassium phenoxide, magnesium methoxide, magnesium ethoxide, magnesium phenoxide, calcium methoxide, calcium ethoxide, calcium phenoxide, aluminium isopropoxide, carboxylates such as sodium formate, sodium acetate, sodium benzoate, calcium formate, calcium acetate, carbonates such as sodium carbonate, potassium carbonate, calcium carbonate, magnesium carbonate, $(NH_4)CO_3$, hydrogen carbonates such as $NaHCO_3$, $KHCO_3$ or $NH_4HCO_3$, mixtures of $NH_4HCO_3$ and ammonium carbamate, ammonia, amines such as triethylaamine, diethylamine, ethylamine, trimethylamine, dimethylamine, methylamine and solutions thereof in water or in organic solvents which are immiscible with the reaction medium. Aqueous sodium hydroxide solution is preferably used as base. If a base which forms a two-phase system with the reaction mixture is used, then after the neutralisation the organic phase containing the bisphenol indan is separated off before further water is added to it.

Water is added to the reaction mixture, which is cooled in order to separate the bisphenol indan. The quantity of water added is preferably one quarter to one third of the quantity of the reaction mixture. The reaction mixture is cooled to a temperature within the range of 0° C. to 30° C., preferably 0° C. to 10° C. The reaction mixture is maintained at this temperature preferably for 1 to 200 minutes, particularly preferably 40 to 80 minutes, before the precipitate formed is separated off. This can be effected by the methods known to the person skilled in the art, for example, by filtration, decantation or centrifugation. The precipitate is preferably then washed with an organic solvent, for example, chlorobenzene. It has become apparent that a markedly less coloured product is obtained if the reaction mixture has been neutralised prior to the addition of water.

In a preferred embodiment of the process the precipitate, after having been separated from the reaction mixture, is suspended in water for 5 to 100 minutes at temperatures within the range of 10° C. to 50° C., preferably 20° C. to 30° C. Here the quantity of water used is preferably one to ten times the quantity of precipitate. The precipitate is then separated off once more. In a preferred embodiment, it is then rinsed again at 10° C. to 50° C. with one to ten times the quantity of water. The solid substance obtained is dried, preferably at temperatures of 20° C. to 150° C., particularly preferably at 70° C. to 90° C. Drying takes place preferably under reduced pressure. The crude product thus obtained is subsequently recrystallised from an acetic acid/water mixture.

Hitherto mixtures of benzene and cyclohexane or methanol and water have been used for the purification of the crude bisphenol indan by recrystallisation. The purity of the products thus obtained is still unsatisfactory for use in the industrial production of plastics. It has now been found that bisphenol indan can be obtained in higher purity if the crude product is recrystallised from mixtures of acetic acid and water.

The invention accordingly also provides a process for the purification of bisphenol indan by recrystallisation from acetic acid/water mixtures. These mixtures contain acetic acid and water preferably in the ratio of 1 to 2 up to 3 to 2; they contain particularly preferably 57 to 63% acetic acid.

For the recrystallisation, the crude product can be placed in water. Following the heating to 70° C. to 100° C., acetic acid is added until the solid substance has dissolved. Alternatively, the crude product can also be dissolved directly in an acetic acid/water mixture at 70° C. to 100° C. The product is precipitated out by subsequent cooling. It is also possible first of all to dissolve the crude product in acetic acid at 70° C. to 100° C. and then to precipitate bisphenol indan by means of water. The product is separated off, washed with water and dried, preferably under reduced pressure at temperatures of 20° C. to 150° C.

The crystallisation can be carried out by the methods known to the person skilled in the art, for example, by multiple crystallisation, stepwise crystallisation or precipitation crystallisation.

Owing to its high purity, the bisphenol indan prepared by the process according to the invention is eminently suitable as starting material for the production of high-quality plastics, for example, polycarbonates.

EXAMPLES

Example 1a 40 g of dimeric isopropenylphenol was dissolved in 100 ml chlorobenzene. The reaction mixture was heated to 80° C. and then 0.14 ml $BF_3$ in the form of etherate was added. The reaction solution was heated to boiling and then maintained under reflux for 40 minutes at 132° C. The reaction mixture was cooled to 0° C. to 10° C. and 30 ml water was added thereto. After 60 minutes, the precipitate was separated off and washed with 50 ml chlorobenzene added in portions. 36 g product (corresponding to 90% of the initial weight of isopropenylphenol) having a bisphenol indan content of 90% was obtained.

The residue was suspended in 100 ml water, separated again after 15 minutes and again 100 ml water was added thereto in portions. The product was separated off and dried at 80° C. under a water suction pump. The dried product was recrystallised from acetic acid/water by first of all suspending it in water at 100° C. and then adding to the suspension a quantity of acetic acid sufficient to dissolve the sediment. The product crystallised out during the subsequent cooling. The solid was collected, briefly washed with water and dried at 80° C. under reduced pressure. 24 g (corresponding to 60% of the initial weight of isopropenylphenol) product having a bisphenol indan content of 97.7% was obtained.

Example 1b 800 g of dimeric isopropenylphenol was dissolved in 2000 ml chlorobenzene. The reaction mixture was heated to 80° C. and then 2.8 ml $BF_3$ in the form of etherate was added. The reaction solution was heated to boiling and then maintained under reflux for 40 minutes at 132° C. Then the catalyst in the reaction solution was neutralised by the addition of sodium hydroxide solution (1,164 g NaOH to 300 ml water) at 80° C. The aqueous phase was separated off, the organic phase was cooled to 0° C. to 10° C. and 600 ml water was added thereto. After 60 minutes, the precipitate was separated off and washed with 1000 ml chlorobenzene added in portions. 480 g product (corresponding to 60% of the initial weight of isopropenylphenol) having a bisphenol indan content of 89% was obtained.

The residue was suspended in 1000 ml water, separated again after 15 minutes and again 1000 ml water was added thereto in portions. The product was separated off and dried at 80° C. under a water suction pump. The dried product was recrystallised from acetic acid/water by dissolving it in an acetic acid/water mixture at 100° C. The product crystallised out during the subsequent cooling. The solid was collected, briefly washed with water and dried at 80° C. under reduced pressure. 312 g (corresponding to 65% of the weight of crude product) product having a bisphenol indan content of 97.2% was obtained.

Example 2 (Comparison example similar to U.S. Pat. No. 3,288,864)

40 g of dimeric isopropenylphenol was dissolved in 100 ml toluene. The reaction mixture was heated to 80° C. and then 0.14 ml $BF_3$ in the form of etherate was added. The reaction solution was then heated at 85° C. for 40 minutes, then cooled to 0° C. to 10° C. and 30 ml water was added thereto. After 60 minutes, the precipitate was separated off and washed with 50 ml toluene added in portions. The residue was suspended in 100 ml water, separated again after 15 minutes and again 2 l water was added thereto in portions. After separation once more and drying under reduced pressure at 80° C., 36 g product (corresponding to 90% of the initial weight of isopropenylphenol) having a bisphenol indan content of 83% was obtained. After recrystallisation from methanol/water, 18 g (corresponding to 45% of the initial weight of isopropenylphenol) product having a bisphenol indan content of 92% was obtained.

Example 3a 50 g crude bisphenol indan (mp 186° C., bisphenol indan content 86.4%) was suspended in 200 ml water. 150 ml acetic acid was added thereto at boiling heat. From the clear solution obtained it was possible to isolate, after cooling, 34 g product (68%) having a bisphenol indan content of 93.2%.

Example 3b 50 g of the crude bisphenol indan was dissolved at boiling heat in a mixture of 79.8 ml water and 60.2 ml acetic acid. After cooling, 31.5 g product (63%) having a bisphenol indan content of 93.5% was obtained.

Example 3c (Comparison)

50 g of the crude bisphenol indan was suspended in 100 ml water. 95 ml methanol was added thereto under reflux. From the clear solution it was possible to isolate, after cooling, 38.4 g product (76.8%) having a bisphenol indan content of 88.8%.

What is claimed is:

1. A process for preparing purified 3-(4-hydroxyphenyl)-1,1,3-trimethylindan-5-ol comprising
   (a) forming a reaction mixture by dissolving at least one member selected from the group consisting of isopropenylphenol, a dimer of isopropenylphenol and an oligomer of isopropenylphenol in an organic solvent having a boiling temperature of 110 to 150° C.,
   (b) heating the reaction mixture to a temperature within the range of 60 to 110° C.,
   (c) adding to the reaction mixture an acid catalyst in an amount of 0.002 to 5% relative to the weight of said member,
   (d) heating the reaction mixture to boiling to allow reaction at the boiling temperature for 1 to 600 minutes,
   (e) optionally neutralizing the reaction mixture at a temperature within the range of 60 to 100° C., by adding a base,
   (f) adding water to the reaction mixture and cooling it to a temperature within the range of 0 to 30° C., to form a precipitate,
   (g) separating off and drying said precipitate and recrystallizing said precipitate from its solution in a mixture of acetic acid and water.

2. Process according to claim 1, wherein the precipitate, after having been separated from the reaction mixture, is suspended in water for 5 to 100 minutes at temperatures within the range of 10° C. to 50° C., then dried and recrystallised.

* * * * *